United States Patent
Liu et al.

(10) Patent No.: US 8,594,792 B2
(45) Date of Patent: Nov. 26, 2013

(54) IMPLANTABLE LEAD AND CORONARY VENOUS PRESSURE SENSOR APPARATUS AND METHOD

(71) Applicants: Lili Liu, Maple Grove, MN (US); Mohan Krishnan, Shoreview, MN (US); Bruce A Tockman, Scandia, MN (US); David R. Wulfman, Minneapolis, MN (US)

(72) Inventors: Lili Liu, Maple Grove, MN (US); Mohan Krishnan, Shoreview, MN (US); Bruce A Tockman, Scandia, MN (US); David R. Wulfman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/690,068

(22) Filed: Nov. 30, 2012

(65) Prior Publication Data

US 2013/0090701 A1    Apr. 11, 2013

Related U.S. Application Data

(62) Division of application No. 12/539,832, filed on Aug. 12, 2009, now Pat. No. 8,340,767.

(60) Provisional application No. 61/088,270, filed on Aug. 12, 2008.

(51) Int. Cl.
    *A61N 1/365*    (2006.01)

(52) U.S. Cl.
    USPC .......................................................... 607/23

(58) Field of Classification Search
    USPC .................................................... 607/23–25
    See application file for complete search history.

(56) References Cited

U.S. PATENT DOCUMENTS

| | | | |
|---|---|---|---|
| 4,329,993 A | 5/1982 | Lieber et al. | |
| 4,601,706 A | 7/1986 | Aillon | |
| 4,602,645 A | 7/1986 | Barrington et al. | |
| 4,708,143 A | 11/1987 | Schroeppel | |
| 4,967,755 A | 11/1990 | Pohndorf | |
| 5,129,394 A | 7/1992 | Mehra | |
| 6,398,738 B1 | 6/2002 | Millar | |
| 6,666,826 B2 * | 12/2003 | Salo et al. | 600/485 |
| 6,892,095 B2 | 5/2005 | Salo | |
| 6,936,040 B2 | 8/2005 | Kramm et al. | |

(Continued)

FOREIGN PATENT DOCUMENTS

JP    59115056 A    7/1984
WO    WO03037423 A1    5/2003

OTHER PUBLICATIONS

International Search Report and Written Opinion issued in PCT/US2009/053535, mailed Oct. 8, 2009, 16 pages.

*Primary Examiner* — George Evanisko
(74) *Attorney, Agent, or Firm* — Faegre Baker Daniels LLP

(57) ABSTRACT

A cardiac rhythm management system comprises a medical electrical lead, a pressure sensing element, and an implantable pulse generator. The lead is sized to be advanced through the right atrium and coronary sinus into a coronary vein adjacent to the left ventricle. The lead includes an opening intermediate its proximal and distal ends, and a lumen extending longitudinally within the body in communication with the opening. The pressure sensing element is movably disposed in lead lumen and is dimensioned to extend through the opening in the lead, and includes a flexible, elongated conductive member having a distal end, and a pressure transducer coupled to the distal end of the conductive member. The pulse generator is configured to receive cardiac rhythm signals from the electrode and fluid pressure signals from the pressure transducer.

11 Claims, 6 Drawing Sheets

(56) References Cited

U.S. PATENT DOCUMENTS

| | | |
|---|---|---|
| 6,970,742 B2 | 11/2005 | Mann et al. |
| 6,988,007 B1 | 1/2006 | Morgan et al. |
| 7,198,603 B2 | 4/2007 | Penner et al. |
| 7,318,264 B2 | 1/2008 | Schugt |
| 8,287,458 B2 * | 10/2012 | Vanney et al. ................ 600/486 |
| 8,340,767 B2 | 12/2012 | Liu et al. |
| 2002/0111662 A1 | 8/2002 | Iaizzo et al. |
| 2003/0130581 A1 | 7/2003 | Salo et al. |
| 2004/0138571 A1 | 7/2004 | Salo et al. |
| 2004/0172077 A1 | 9/2004 | Chinchoy |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0293714 A1 | 12/2006 | Salo et al. |
| 2007/0129764 A1 * | 6/2007 | Burnes ........................... 607/18 |
| 2009/0270741 A1 | 10/2009 | Vanney et al. |

* cited by examiner

IMPLANTABLE LEAD AND CORONARY VENOUS PRESSURE SENSOR APPARATUS AND METHOD

CROSS-REFERENCE TO RELATED APPLICATION

This application is a divisional application of U.S. application Ser. No. 12/539,832, filed Aug. 12, 2009, entitled "IMPLANTABLE LEAD AND CORONARY VENOUS PRESSURE SENSOR APPARATUS AND METHOD," which claims the benefit of U.S. Provisional Application No. 61/088,270, filed Aug. 12, 2008, entitled "IMPLANTABLE LEAD AND CORONARY VENOUS PRESSURE SENSOR APPARATUS AND METHOD," both of which are herein incorporated by reference in their entireties.

TECHNICAL FIELD

The present invention systems and methods for heart failure treatment, and in particular, systems and methods for measuring blood pressure in a coronary vein during one or more heart cycles, and using the information in cardiac rhythm management and/or heart failure treatment.

BACKGROUND

Various measures have been identified for estimating and evaluating reduced cardiac function. Such measures include left ventricular pressure (LVP), which can be useful in estimating and evaluating cardiac hemodynamic performance. Direct measurement of LVP requires locating one or more pressure sensors directly in the left ventricle, which can be technically and clinically challenging.

SUMMARY

The present invention, in one embodiment, is a cardiac rhythm management system comprising a medical electrical lead, a pressure sensing element, and an implantable pulse generator. The lead includes an elongated, flexible body made of an electrically insulative material. The body has a proximal end and distal end, and is sized to permit the distal end to be advanced through a right atrium and coronary sinus and into a first coronary vein adjacent to a left ventricle of a patient's heart. The lead further includes a first opening in the body at a point intermediate the proximal and distal ends, a lumen extending longitudinally within the lead body and in communication with the first opening, and at least one electrode coupled to the lead body proximate the distal end. The pressure sensing element is movably disposed at least partially in the lead lumen and has a distal end portion dimensioned to be extendable through the opening and to be positioned in the first coronary vein or a second coronary vein adjacent to the left ventricle of the patient's heart. The pressure sensing element includes a flexible, elongated conductive member electrically insulated over a substantial portion of its length, a pressure transducer fixedly and operatively coupled to the conductive member in the distal end portion of the pressure sensing element. The pulse generator includes a detection/energy delivery system coupled to the lead and the pressure sensing element. The detection/energy delivery system is configured to receive cardiac rhythm signals from the at least one electrode and fluid pressure signals from the pressure transducer, and to deliver an electrical signal to the at least one electrode.

In another embodiment, the present invention is a cardiac rhythm management system comprising a medical electrical lead, a pressure sensing element, and an implantable pulse generator. The lead includes an elongated, flexible body made of an electrically insulative material. The lead body has a proximal end and distal end, and is sized to permit the distal end to be advanced through a right atrium and coronary sinus and into a first coronary vein adjacent to a left ventricle of a patient's heart. The lead further includes a first opening in the body at a point intermediate the proximal and distal ends, a lumen extending longitudinally within the lead body and in communication with the first opening, and at least one electrode coupled to the lead body proximate the distal end. The pressure sensing element is movably disposed at least partially in the lead lumen and has a distal end portion dimensioned to be positioned within the lumen adjacent to the opening. The pressure sensing element includes a flexible, elongated conductive member electrically insulated over a substantial length portion of its length, and a pressure transducer fixedly and operatively coupled to the conductive member in the distal end portion of the pressure sensing element. The pressure transducer is further locatable adjacent to the opening. The implantable pulse generator includes a detection/energy delivery system coupled to the lead and the pressure sensing element. The detection/energy delivery system is configured to receive cardiac rhythm signals from the at least one electrode and fluid pressure signals from the pressure transducer, and to deliver an electrical signal to the at least one electrode.

In yet another embodiment, the present invention is a method of optimizing implant parameters for an implantable cardiac rhythm management system including an implantable pulse generator and a coronary venous lead, the coronary venous lead including an elongate lead body and at least one pace/sense electrode coupled to the body. The method comprises first positioning the electrode within a first coronary vein adjacent a left ventricle of a heart, and then operatively coupling the electrode to the implantable pulse generator or a pacing system analyzer device. The method further includes deploying a pressure transducer at a first location in the first coronary vein or a second coronary vein, and generating an acute baseline pressure waveform based on an output signal from the pressure transducer over a plurality of cardiac cycles. The method further comprises applying an electrical stimulus to the left ventricle through the electrode using the implantable pulse generator or the pacing system analyzer, and adjusting one or more CRM system parameters while monitoring changes in the pressure waveform relative to the baseline.

In yet another embodiment, the present invention is a method of chronically detecting the onset of early decompensation in a patient suffering from congestive heart failure. The method comprises generating a first coronary venous pressure waveform using a pressure transducer chronically implanted in a coronary vein, estimating at least one first hemodynamic parameter value based on the first coronary venous pressure waveform, and initiating a cardiac rhythm management (CRM) therapy. The method further comprises generating a second coronary venous pressure waveform at a predetermined time after initiation of the CRM therapy, and estimating at least one second hemodynamic parameter value based on the second coronary venous pressure waveform. The method further comprises comparing the first and second hemodynamic parameter values, and comparing the difference between the first and second hemodynamic parameter values and a predetermined threshold value to identify an onset of early decompensation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
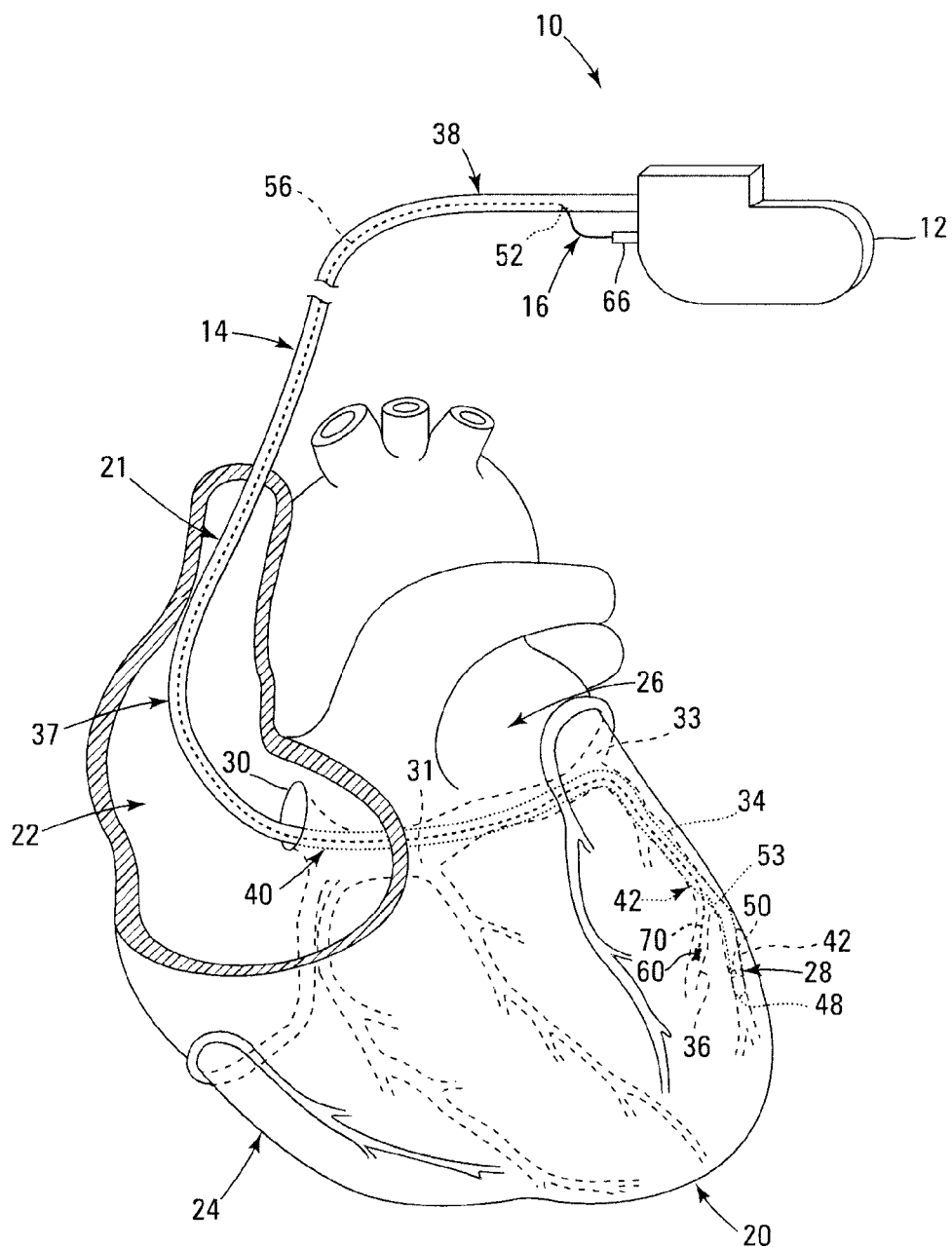
FIG. 1A is a schematic illustration of a cardiac rhythm management (CRM) system according to one embodiment of the present invention in a deployed configuration.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A is a schematic view of a cardiac rhythm management (CRM) system 10 according to one embodiment of the present invention. As shown in FIG. 1A, the CRM system 10 includes a pulse generator 12, a medical electrical lead 14, and a pressure sensing element 16, which are shown in FIG. 1A in a deployed configuration with respect to a patient's heart 20. As is known in the art, the heart 20 includes a right atrium 22 and a right ventricle 24, a left atrium 26 and a left ventricle 28, a coronary sinus ostium 30 in the right atrium 22, a coronary sinus 31, and various coronary veins including a great cardiac vein 33 and an exemplary branch coronary veins 34 and 36. In the illustrated embodiment, the lead 14 and the pressure sensing element 16 are partially deployed in the coronary veins 34 and 36, respectively. As will be appreciated, the pulse generator 12 is typically implanted subcutaneously at an implantation location in the patient's chest or abdomen.

Figure 1B:
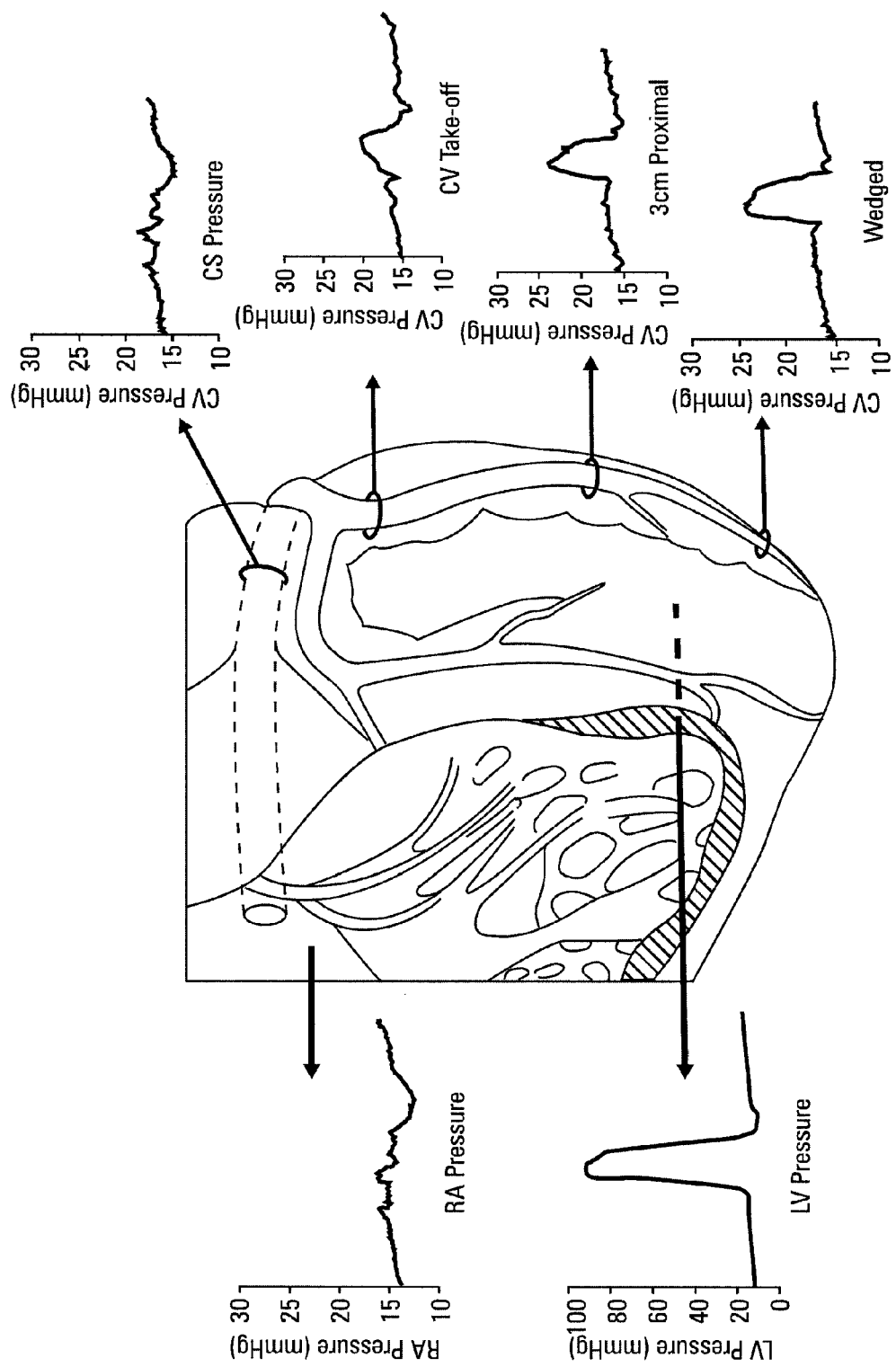
FIG. 1B is an illustration of coronary venous system pressure waveforms that can be obtained utilizing the CRM system of FIG. 1A.

The CRM system 10 according to various embodiments of the present invention uses a pressure parameter reading obtained from within the coronary venous system to diagnose medical conditions, such as the onset of early decompensation in a patient with congestive heart failure, and/or to optimize patient therapy. In various embodiments, the pressure parameter reading is utilized to provide an estimate of left ventricular pressure (LVP), which is a useful measure as an indicator of cardiac function. FIG. 1B illustrates pressure waveforms obtained from the right atrium (RA), left ventricle (LV), coronary sinus (CS) and various locations in a coronary vein (CV). As shown, the CV waveform takes on the same general shape as the LV waveform, particularly where the CV pressure is taken from a location lower in the coronary vein.

In particular, the left ventricular end diastolic pressure (LVEDP) is an especially important measure used to evaluate hemodynamic state. LVEDP can be estimated utilizing pressure data obtained from within a coronary vein without requiring direct pressure readings from the left ventricle or left atrium. Changes in LVEDP (and other indicators of hemodynamic state) over time can be utilized, according to various embodiments of the present invention, to adjust and optimize therapy parameters for the CRM system 10.

As shown in FIG. 1A, the lead 14 includes an elongate body 37 defining a proximal region 38 and a distal region 40. The distal region 40 has a distal end portion 42 terminating in a distal tip 48. The lead 14 further includes at least one electrode 50 operatively coupled to at least one conductor (not shown in FIG. 1A) extending through the lead body 37. Additionally, the lead 14 includes a proximal opening 52 through the lead body 37 in the proximal region 38, and a distal opening 53 through the lead body 37 in the distal region 40. In the embodiment illustrated in FIG. 1A, the distal region 40 is guided through the superior vena cava 21, the right atrium 22, the coronary sinus ostium 30, and the coronary sinus 31, and into the coronary vein 34, with the distal end portion 42 positioned therein.

The illustrated position of the lead 14 may be used, for example, for sensing physiologic parameters and delivering a pacing and/or defibrillation stimulus to the left side of the heart 20. The lead 14 may also be partially deployed in other coronary veins such as the great cardiac vein 33 or other branch vessels for providing therapy to the left side (or other portions) of the heart 20. In various embodiments, the lead 14 may be configured in substantially the same or an identical manner as conventional coronary venous leads for cardiac resynchronization therapy, bi-ventricular pacing, and the like, modified as described herein to facilitate sensing and measuring coronary vein pressure parameters.

The lead 14 is illustrated as including a single electrode 50, although it will be appreciated that in other embodiments, the lead 14 may be a multi-electrode lead, i.e., including a plurality of electrodes 50 so as to be operable in a multi-polar pace/sense configuration. Additionally, in various embodiments, multi-electrode leads 14 can facilitate selectively changing the pacing site within the coronary vein 34 by selecting different ones of the plurality of electrodes 50 to operate as the active electrodes through which cardiac rhythm signals are sensed and electrical stimuli are applied to the left ventricle.

As further shown in FIG. 1A, the pressure sensing element 16 includes an elongated, flexible conductive member 56 and a pressure transducer 60. The conductive member 56 has a proximal end 66 coupled to the pulse generator 12, and a distal end 70 opposite the proximal end 66. As shown, the pressure transducer 60 is coupled to the distal end 70 of the conductive member 56. As further shown, in the illustrated embodiment, the pressure sensing element 16 extends through the proximal opening 52 and longitudinally within the lead body 37, and exits the lead body 37 through the distal opening 53.

The pressure transducer 60 is operable to sense and to generate an electrical signal representative of a fluid pressure parameter within the coronary vein 36 in which it is implanted. The conductive member 56 operatively couples the pressure transducer 56 and associated components within the pulse generator 12, and thus is electrically insulated along its length.

In the illustrated embodiment, the pressure transducer 60 is disposed, in its implanted state, in the coronary vein 36 while the lead electrode 50 is positioned in the coronary vein 34. As will be explained below, in other embodiments, the lead electrode 50 and the pressure transducer 60 are disposed in the same coronary vein. Thus, the CRM system 10 according to the various embodiments disclosed herein provide for a range of implantation configurations for the lead 14 and the pressure transducer 16, which in turn provides wide flexibility in implanting the CRM system 10 so as to provide optimal therapeutic performance.

The pulse generator 12 may be any implantable medical device known in the art or later developed, for delivering an electrical therapeutic stimulus to the patient. In one embodiment, the pulse generator 12 is a pacemaker. In one embodiment, the pulse generator 12 is a cardiac resynchronization (CRT) device configured for bi-ventricular pacing and sensing. In another embodiment, the pulse generator 12 is an implantable cardiac defibrillator. In still other exemplary embodiments, the pulse generator 12 includes combinations of pacing, CRT, and defibrillation capabilities. While not shown in FIG. 1A, it will be appreciated that the pulse generator 12 includes hardware, software, and circuitry operable as a detection/energy delivery system configured to receive cardiac rhythm signals from the lead electrode 50 and pressure signals from the pressure transducer 60, and also to deliver a therapeutic electrical signal to the electrode 50.

As will be appreciated, in various embodiments, the CRM system 10 further includes additional leads deployed in, for example, the right atrium 22 and/or right ventricle 24, which leads may include one or more enlarged coil electrodes for delivering relatively high voltage shocking stimuli (e.g., for defibrillation and/or cardioversion therapy). Accordingly, the CRM system 10 may, in various embodiments, be configured for CRT and/or CRT-D (cardiac resynchronization with defibrillation) therapy, as is known in the art.

Figure 2A:
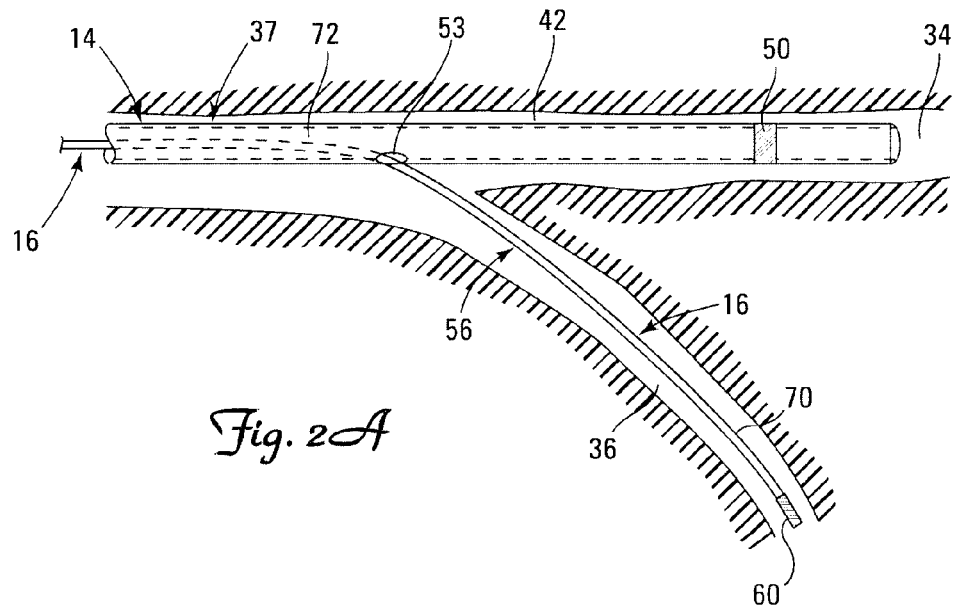
FIGS. 2A and 2B are schematic illustrations of a medical electrical lead and pressure sensing element of the CRM system of FIG. 1A in implanted configurations according to one embodiment of the present invention.
Figure 2B:
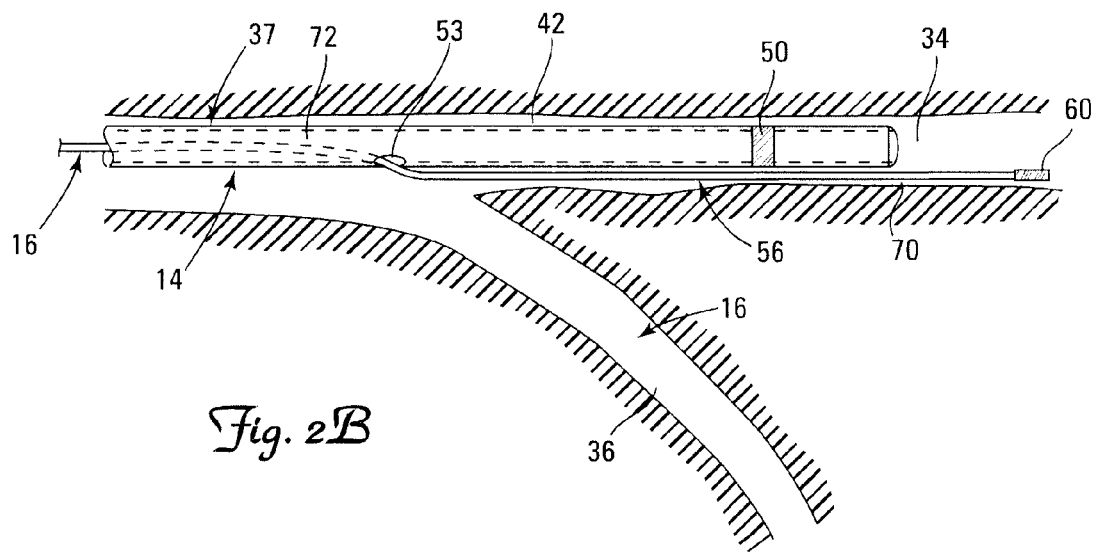

FIGS. 2A and 2B are schematic illustrations of portions of the lead 14 and the pressure sensing element 16 in alternative implanted configurations according to one embodiment of the present invention. As shown in FIG. 2A, in one embodiment, the distal end portion 42 of the lead 14 is implanted in the coronary vein 34. As further shown, the lead 14 includes an internal lumen 72 in communication with the distal opening 53, and the conductive member 56 of the pressure sensing element 16 is partially disposed within the lumen 72 with the distal end 70 of the conductive member 56 exiting through the distal opening 53 such that the pressure transducer 60 is located external to the lumen 72. Additionally, in the embodiment of FIG. 2A, the pressure transducer 60 is located in the coronary vein 36 while the electrode 50 of the lead 14 is located in the coronary vein 34. Accordingly, the configuration of FIG. 2A provides for sensing cardiac rhythm signals and applying electrical stimuli to the left ventricle from within one coronary vein, while at the same time sensing a coronary vein pressure parameter in another vein.

In FIG. 2B, the pressure sensing element 16 is also partially disposed in the lumen 72 with the distal end 70 of the conductive member 56 exiting through the distal opening 53 such that the pressure transducer 60 is located external to the lumen 72. In contrast to FIG. 2A, however, in the embodiment of FIG. 2B, the lead electrode 50 and the pressure transducer 60 are both disposed in the same coronary vein 34. Thus, the ability to dispose the pressure sensing element 16, and in particular, the pressure transducer 60 through the lead body 37 at a location proximal to the distal tip of the lead 14 provides a range of options regarding the relative implantation locations of the lead electrode 50 and the pressure transducer 60. Depending on the particular therapeutic needs of the patient or requirements imposed by the patient's coronary anatomy, e.g., the condition and/or tortuosity of the target coronary veins, the configuration of FIG. 2A may be advantageous over the configuration of FIG. 2B, and vice versa. Thus, the configuration of the lead 14 and the pressure sensing element 16 provide significant flexibility to the implanting technician and/or physician.

As will be appreciated, although the distal opening 53 is located proximal to the electrode 50 in FIGS. 2A and 2B, in various other embodiments, the opening 53 is located distal to the electrode 50 but still proximal to the lead distal tip. As will further be appreciated, in various embodiments, the lead 14 may include additional electrodes 50. Additionally, regardless of the relative positions of the distal opening 53 and the electrode 50, the relative location of the pressure transducer 60 and the electrode 50 can be selectively varied by extending or retracting the pressure transducer 60 as appropriate.

The pressure transducer 60 can be any device, whether now known or later developed, suitable for sensing pressure parameters within the coronary venous system and generating and transmitting a signal indicative of such pressure parameters to another device, e.g., the pulse generator 12. In various embodiments, the pressure transducer 60 is configured to sense and generate a signal indicative of hydrostatic pressure within the coronary vein. In various embodiments, the pressure transducer 60 can be a micro-electrical-mechanical system (MEMS) device, which as will be appreciated, utilizes semiconductor techniques to build microscopic mechanical structures in a substrate made from silicon or similar materials. In various embodiments, the pressure transducer 60 can include a micro-machined capacitive or piezoresistive transducer exposed to the bloodstream. Other pressure transducer technologies, such as resistive strain gages, are known in the art and can also be employed as a pressure transducer 60.

In other exemplary embodiments, the pressure transducer 60 can include one or more piezoelectric elements. As will be appreciated, such piezoelectric elements are configured to flex and/or deflect in response to changes in pressure within the coronary vein in which it is implanted, and to generate an output current or voltage proportional to the corresponding pressure change. In such embodiments, the pressure transducer 60 may advantageously be configured to sense fluid characteristics indicative of changes in coronary venous pressure during the cardiac cycle, e.g., dp/dt, which in turn can be monitored over time.

The pressure transducer 60 is coupled to the conductive member 56, which operates to convey electrical signals generated by the transducer 60 indicative of the sensed pressure parameter, and depending on the transducer technology employed, to provide operating power to the pressure transducer 60.

In various embodiments, pressure sensing element 16, and in particular, the conductive member 56, is configured to provide much the same feel and handling characteristics as a conventional guide wire or stylet. Thus, the pressure sensing element 16 can be deployed through the lumen 72 in a manner substantially similar to a stylet, which may advantageously assist the physician in implanting the lead 14.

Of course, either of the leads 14, 114 can, in various embodiments, include a plurality of openings located at selected positions along the respective lead bodies so as to permit even more selectivity as to the relative implantation locations for the electrode 50 and the pressure transducer 60.

Figure 3A:
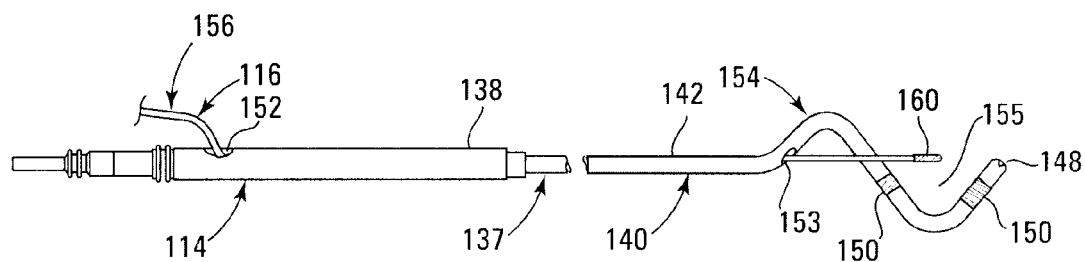
FIGS. 3A and 3B are schematic illustrations of an alternative lead and pressure sensing element for use with the CRM system of FIG. 1A according to another embodiment of the present invention.
Figure 3B:
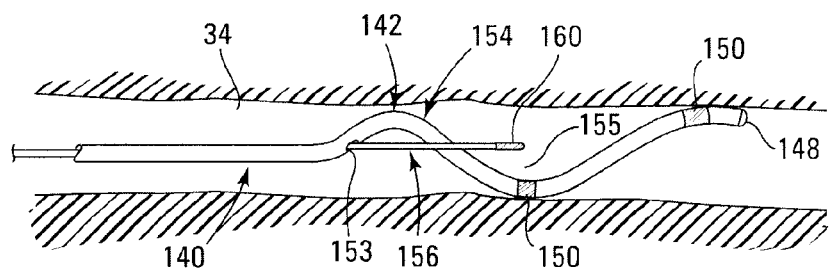

FIGS. 3A and 3B are schematic illustrations of portions of an alternative lead 114 and pressure sensing element 116 for use with the CRM system of FIG. 1A according to another embodiment of the present invention. FIG. 3A shows the lead 114 in an un-implanted state, while FIG. 3B illustrates a portion of the lead 114 implanted in the coronary vein 34. As shown in FIGS. 3A and 3B, the lead 114 includes an elongate body 137 defining a proximal region 138 and a distal region 140. The distal region 140 has a distal end portion 142 terminating in a distal tip 148. The lead 114 further includes at least one electrode 150 operatively coupled to at least one conductor (not shown in FIG. 1A) extending through the lead body 137. Additionally, the lead 14 includes a proximal opening 152 through the lead body 137 in the proximal region 138, and a distal opening 153 through the lead body 137 in the distal region 140. As will be appreciated, the lead 114 further includes an internal lumen (not shown) extending longitudinally within the lead body 137 between the proximal and distal regions 138, 140. Additionally, as with the lead 14 described above, the distal opening 153 is in communication with the lumen. As further shown, particularly in FIG. 3A, the lead 114 includes a pre-formed portion 154 of the distal region 140, which assumes a helical shape defining an interior space 155.

The pressure sensing element 116 includes an elongated, flexible conductive member 156 and a pressure transducer 160, and can generally be constructed in a manner similar or identical to the pressure sensing element 116 described above. As shown, in the illustrated embodiment, the pressure sensing element 116 extends through the proximal opening 152 and longitudinally within the lead body 137, and exits the lead body 137 through the distal opening 153 such that the pressure transducer 160 is located external to the lead 114. As further shown, the pressure transducer 160 is advantageously located within the internal space 155 defined by the helical pre-formed portion 154 of the lead 114.

Although in the embodiments described above the pressure sensing elements 16, 116 include only a single pressure transducer 60, 160, in various other embodiments, the pressure sensing elements can include multiple pressure transducers along their lengths. In such embodiments, the pressure sensing elements are capable of simultaneously sensing coronary vein pressure at different locations adjacent to the left ventricle.

Figure 4:
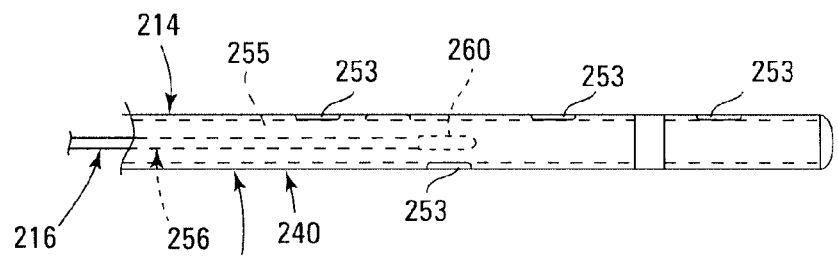
FIG. 4 is a schematic illustration of an alternative lead and pressure sensing element for use with the CRM system of FIG. 1A according to another embodiment of the present invention.

FIG. 4 is a schematic illustration of a distal end portion of an alternative lead 214 and pressure sensing element 216 assembly for use with the CRM system of FIG. 1A according to another embodiment of the present invention. As shown in FIG. 4, the lead 214 includes a lead body 237 defining, in part, a distal region 240. The lead 214 can, in general, be configured in substantially the same or an identical manner as the leads 14 and 114 described above. In the illustrated embodiment, the lead 214 includes a plurality of openings 253 in the distal region 240 which, like the openings 53, 153 in the leads 14, 114 described above, are in communication with an internal lumen 255. As further shown, the pressure sensing element 216 includes an elongated conductive element 256 and a pressure transducer 260 coupled thereto. In the embodiment of FIG. 4, the pressure transducer 260 is disposed within the lead lumen 255 at a location adjacent one of the openings 253 which, in effect, operates as a conduit for permitting the transducer 260 to sense a fluid pressure parameter within the target coronary vein. Including a plurality of openings 253 can provide desirable flexibility as to the location of the pressure transducer 260. For example, if one of the openings 253 is occluded by a blood clot or fibrotic tissue, or if the opening 253 is pressed against the coronary vein wall so as to inhibit fluid communication through the opening 253, the pressure transducer 260 can be positioned adjacent to a different opening 253. Again, as explained above, either of the leads 14, 114 could also include a plurality of openings 53, 153.

In a variation of the lead 214, in various embodiments, the pressure transducer 260 can be extended so as to be positioned within the lumen 255 proximate the distal opening of the lumen 255 (i.e., the opening through which a guide wire extends in an over-the-wire delivery technique). In such embodiments, the distal opening of the lumen 255 can also operate as a conduit for permitting the transducer 260 to sense fluid pressure parameters within the coronary vein in which the lead 214 is implanted. In various such embodiments, the lead 214 can also include the openings 253 in addition to the distal opening in the lumen 255, or alternatively, the additional openings 253 can be omitted.

Any of the leads 14, 114, 214 described above can, in various embodiments, include an occlusion device on the lead body. In some circumstances, partially or fully occluding the coronary vein in which the lead is implanted is desirable. Exemplary occlusion devices are disclosed, for example, in commonly assigned U.S. Patent Application Publication No. 2004/0138571 titled "Method and Apparatus for Adjusting Interventricular Delay Based on Ventricular Pressure," the entire disclosure of which is incorporated by reference. The occlusion device, if present, can be located proximal or distal to the respective openings in the lead body. It is emphasized, however, that occlusion of the target coronary vein is not a requirement for the operation of the CRM system 10.

Figure 5:
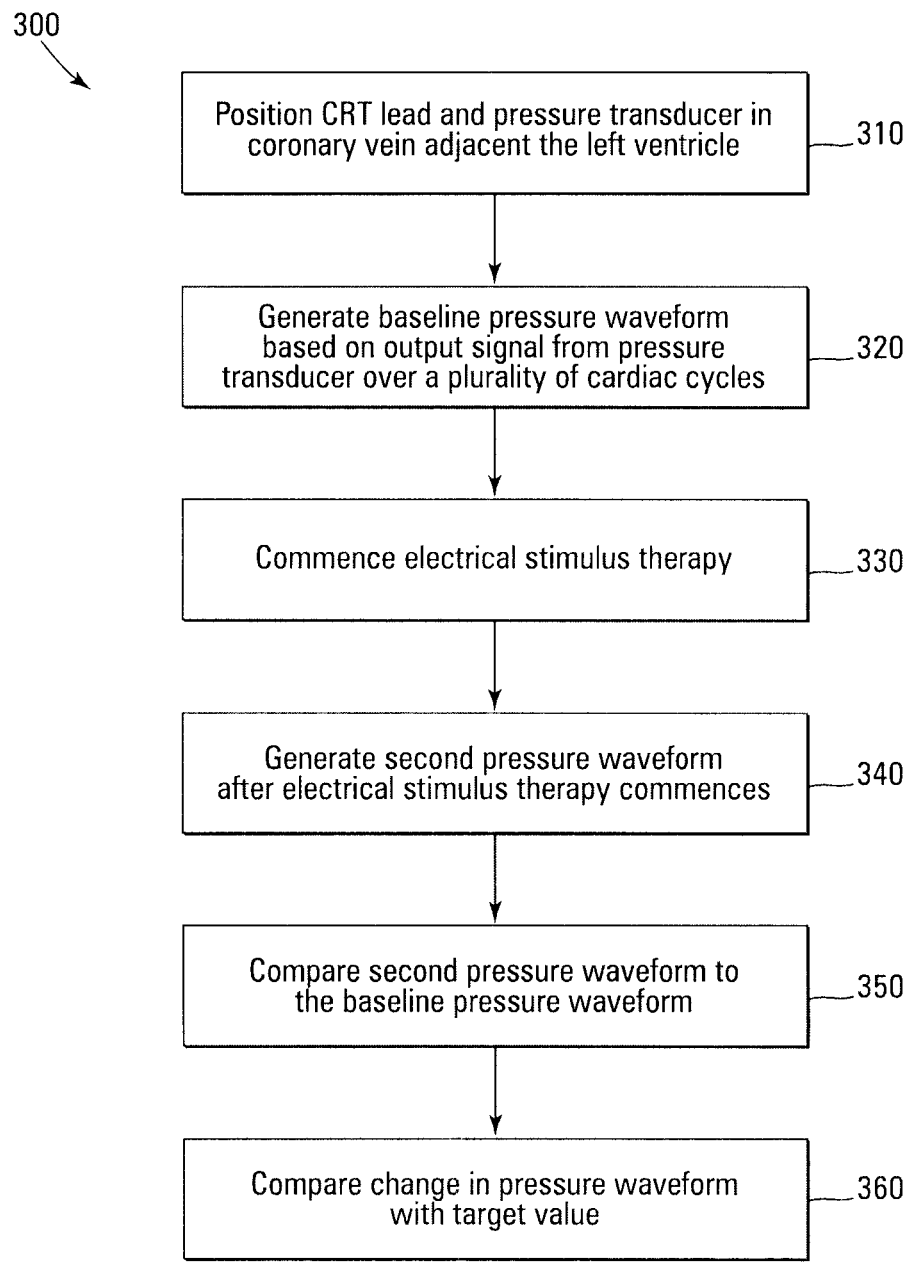
FIG. 5 is a flow chart illustrating a method of using the CRM system of FIG. 1A including chronically adjusting CRM system parameters according to one embodiment of the present invention.

FIG. 5 is a flow chart illustrating a method 300 of using the CRM system of FIG. 1A for chronic therapy optimization according to one embodiment of the present invention. As shown in FIG. 5, a lead and pressure transducer are positioned in a coronary vein adjacent to left ventricle patient's heart. (block 310) Various methods and systems, e.g., guide catheters, guide wires for over-the-wire leads, stylets, and combinations thereof, for implanting left ventricular leads in the coronary venous system are well known, and need not be discussed in detail here. It is emphasized, however, that the lead can be implanted using any techniques and devices, whether now known or later developed. The pressure transducer can be deployed in the same coronary vein as the lead electrode(s), or a different coronary vein, as discussed above. Additionally, the pressure transducer can be deployed through the lead lumen and positioned external to the lead, or alternatively, can be positioned adjacent to one of the openings in the lead body, as also discussed above.

Next, a baseline pressure waveform is generated based on an output signal from the pressure transducer over a plurality of cardiac cycles. (block 320) Electrical therapy to the heart, e.g., cardiac resynchronization therapy, is then commenced using an implantable pulse generator. (block 330)

After electrical therapy has commenced, a second coronary vein pressure waveform is generated. (block 340) The second pressure waveform is then compared to the baseline pressure waveform. (block 350) Then, the difference between the second pressure waveform and the baseline pressure waveform can be utilized in numerous ways to modify and thereby optimize patient therapy. As shown, in one embodiment, the difference between the second pressure waveform and the baseline pressure waveform is compared to a target value. (block 360) This can be repeated at desired intervals as appropriate. In various exemplary embodiments, one or more therapy parameters can be modified if the change in the blood pressure waveform relative to the baseline exceeds a pre-determined threshold value. Alternatively, the comparison between the second, post-therapy pressure waveforms and the baseline pressure waveforms can be monitored substantially continuously through an advanced patient management (APM) system, such as the LATITUDE® system marketed by Boston Scientific Corporation.

As discussed above, it is known that the coronary vein pressure waveform correlates closely to the LVP waveform, and thus can be utilized to estimate LVEDP. Thus, the coronary vein pressure provides a direct measurement of the patient's hemodynamic state. This hemodynamic state data can then be utilized in a number of ways, for example, to detect early decompensation. For example, in various embodiments, a rise in the LVEDP over time relative to the baseline LVEDP can be monitored. If the rise exceeds a pre-determined threshold amount, this can be an indication of the onset of early decompensation. Alternatively or additionally, the length of the pre-ejection period can be monitored in a similar fashion.

Additionally, the pressure data can be processed by the pulse generator and/or a diagnostic device together with other sensor data for more advanced therapy optimization. In some embodiments, the implanted pulse generator processes the pressure and other data and adjusts therapy parameters in a closed loop system. In other embodiments, the coronary vein pressure waveforms (and/or data derived therefrom such as LVEDP), along with other sensor data, are provided to a clinician, who can then adjust therapy parameters accordingly. Examples of pacing therapy parameters that can be adjusted based on the pressure transducer data include, without limitation, A-V delay, V-V delay, electrode and/or pacing site selection (e.g., in a system utilizing a multi-electrode lead whereby the specific pace/sense electrodes being utilized as the active electrodes can be selected within the pulse generator), and/or drug therapy regimens.

The additional sensor data utilized in conjunction with the coronary vein pressure waveform is not intended to be limited. In various embodiments, electrical cardiac rhythm signals sensed at the electrode on the coronary vein leads 14, 114, 214, in addition to or in lieu of right atrial and/or right ventricular lead electrodes, are utilized in conjunction with the coronary vein pressure waveform. Still other sensor data that will be useful in conjunction with the coronary vein pressure waveform are also contemplated within the scope of the present invention.

Additionally, in some circumstances, coronary vein pressure fluctuations are a function of local cardiac wall motion. Thus, changes in coronary vein pressure over time (e.g., LV dp/dt) can provide an estimate of localized heart contractility. In various embodiments, as described above, the pressure transducers employed (e.g., piezoelectric transducers) can sense and generate signals indicative of changes in coronary venous pressure during the cardiac cycle. Additionally, in embodiments utilizing multiple pressure transducers at different locations adjacent to the left ventricle, mechanical timing of heart contractility can also be a useful data set in addition to the coronary vein pressure waveform itself. For example, any of the therapy optimization techniques based on electro-mechanical timing utilizing LVP disclosed in commonly assigned U.S. Patent Application Publication No. 2006/0293714 titled "Method and Apparatus for Controlling Cardiac Therapy Based on Electromechanical Timing," which is incorporated herein by reference in its entirety, may be utilized in conjunction with the present invention.

Figure 6:
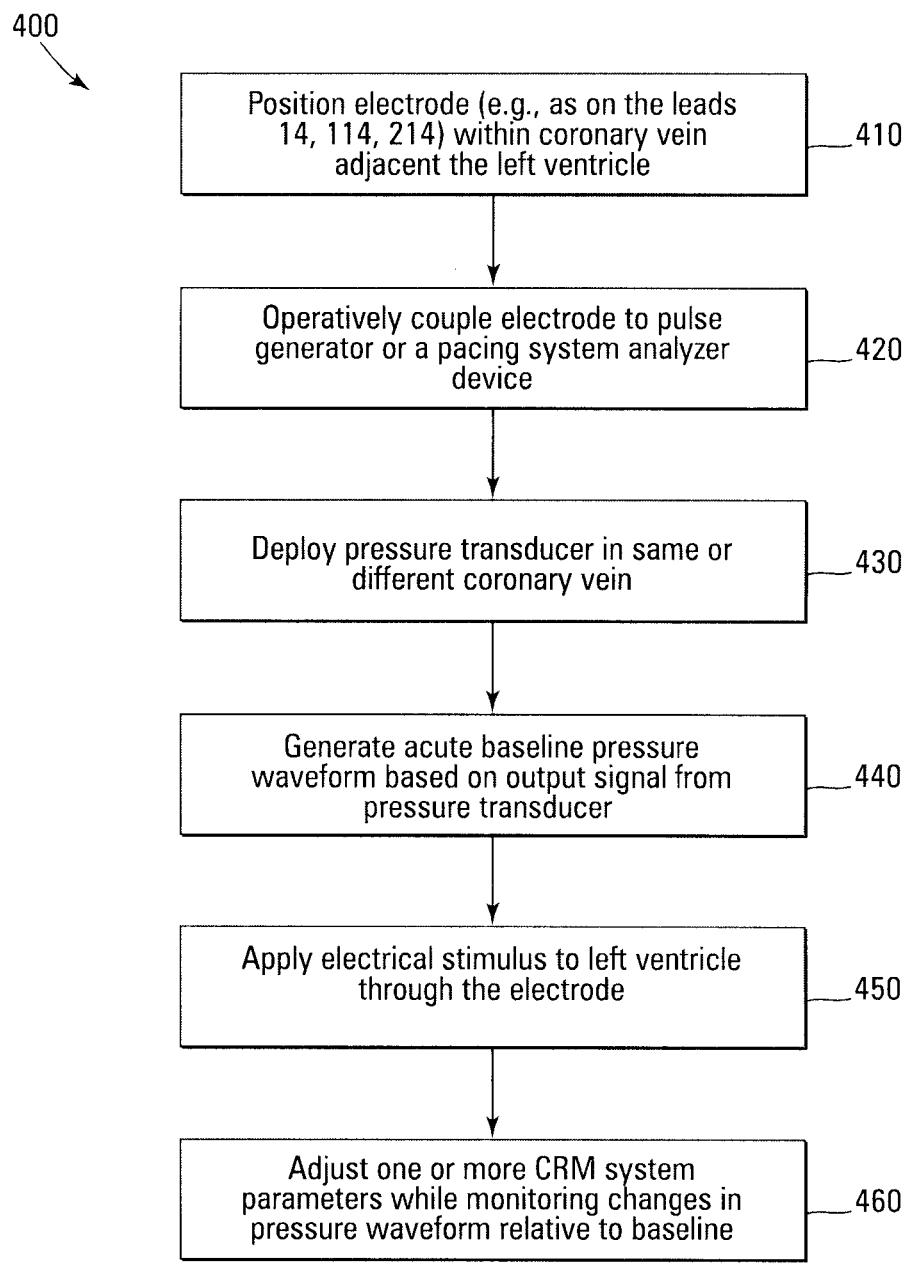
FIG. 6 is a flow chart illustrating a method of acutely optimizing implant parameters for the CRM system of FIG. 1A according to another embodiment of the present invention.

FIG. 6 is a flow chart illustrating a method 400 of optimizing parameters of the CRM system 10 at implant according to another embodiment of the present invention. As shown in FIG. 6, the method 400 includes first positioning an electrode (e.g., as on the leads 14, 114, 214) within a coronary vein adjacent the left ventricle of a heart. (block 410) Here again, lead delivery can be accomplished using any devices and techniques known in the art. Of course, right atrial and/or right ventricular leads can also be implanted at this time. The electrode is operatively coupled to the pulse generator or a pacing system analyzer device. (block 420) A pressure transducer is then deployed into the same coronary vein as the electrode, or into a different coronary vein, as described above. (block 430) In one embodiment, the pressure transducer is deployed through a lumen and out an opening in the lead so as to position the pressure transducer in the coronary vein (or in a different coronary vein). In one embodiment, the pressure transducer is deployed through a lumen of the lead so as to locate the pressure transducer within the lumen adjacent to an opening in the lead. In various embodiments, multiple pressure transducers can be deployed and located in different positions adjacent to the left ventricle.

Next, an acute baseline pressure waveform is generated based on an output signal from the pressure transducer over a plurality of cardiac cycles. (block 440) An electrical stimulus is then applied to the left ventricle through the electrode (and, if desired, to right atrial and/or right ventricular electrodes) using the implantable pulse generator or the pacing system analyzer. (block 450). Finally, the clinician then adjusts one or more CRM system parameters while monitoring changes in the pressure waveform relative to the baseline. (block 460) The CRM system parameters providing the optimal hemodynamic response relative to the baseline can then be selected.

As with the chronic therapy optimization method described above, the CRM system parameters that can be adjusted include, without limitation, A-V delay and/or V-V delay. In addition, the CRM system parameters that can be adjusted include repositioning the electrode within the coronary vein, or relocating the electrode to a different coronary vein. Still additionally, the CRM system parameters that can be adjusted also include electrode and/or pacing site selection (e.g., in a system utilizing a multi-electrode lead whereby the specific pace/sense electrodes being utilized as the active electrodes can be selected within the pulse generator). Still other CRM system parameters that can be adjusted according to the method 400 will be apparent to those skilled in the art based on the foregoing.

Typically, CRM system parameters are selected at implant based on threshold measurements alone. The method 400, in contrast, provides for optimization of CRM system parameters at implantation based on direct information regarding the patient's hemodynamic response to the therapy parameter adjustments.

As will be appreciated, the methods 300, 400 can be carried out utilizing other lead configurations in addition to or in lieu of the leads 14, 114, 214 described above. In various embodiments, a coronary venous lead including one or more pressure transducers fixedly coupled to the lead body can be utilized to carry out the methods 300, 400. Exemplary such leads include, but are not limited to, those described in U.S. Pat. No. 4,708,143 to Schroeppel, et al., and U.S. Pat. No. 4,967,755 to Pohndorf, each of which is incorporated herein by reference in its entirety.

In still other embodiments, one or more wireless pressure sensing elements may be implanted in the coronary venous system adjacent to the left ventricle 28 in addition to or in lieu of the lead-based pressure sensing elements described above. In such embodiments, the wireless pressure sensing element may be coupled to a stent-like fixation device for chronic implantation in the coronary venous system, and can include telemetry components enabling wireless communication (e.g., via RF, inductive, acoustic, or other wireless communication links) between the sensor element and another device (e.g., the pulse generator 12 and/or a reader/programmer located external to the patient). Exemplary wireless sensor systems that could be utilized (or adapted to be utilized) in the foregoing systems are described in U.S. Pat. No. 7,198,603 entitled "Apparatus and Methods Using Acoustic Telemetry for Intrabody Communications," the disclosure of which is incorporated herein by reference in its entirety.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of optimizing implant parameters for an implantable cardiac rhythm management system including an implantable pulse generator and a coronary venous lead, the coronary venous lead including: an elongate, flexible lead body made of an electrically insulative material, the body having a proximal end and a distal end, the body being sized to permit the distal end to be advanced through a right atrium and a coronary sinus and into a first coronary vein adjacent to a left ventricle of a patient's heart; a first opening in the body at a point intermediate the proximal and distal ends; a lumen extending longitudinally within the lead body and in communication with the first opening; and at least one pace/sense electrode coupled to the body proximate the distal end, the method comprising:
    positioning the electrode within the first coronary vein adjacent the left ventricle;
    operatively coupling the electrode to the implantable pulse generator or a pacing system analyzer device;
    deploying a pressure transducer through the lumen and out the first opening in the lead so as to position the pressure transducer in the first coronary vein or a second coronary vein;
    generating an acute baseline pressure waveform based on an output signal from the pressure transducer over a plurality of cardiac cycles;
    applying an electrical stimulus to the left ventricle through the electrode using the implantable pulse generator or the pacing system analyzer; and
    adjusting one or more CRM system parameters while monitoring changes in the pressure waveform relative to the baseline.

2. The method of claim 1 wherein adjusting one or more CRM system parameters includes relocating the electrode to a second location within the first coronary vein, the second coronary vein, or a third coronary vein.

3. The method of claim 1 wherein adjusting one or more CRM system parameters includes adjusting A-V delay and/or V-V delay.

4. The method of claim 1 wherein adjusting one or more CRM system parameters further includes adjusting one or more CRM system parameters while monitoring changes in mechanical timing in addition to changes in the pressure waveform relative to the baseline.

5. The method of claim 1 wherein a portion of the lead is pre-formed into a helical shape defining an interior space, and wherein the pressure transducer is deployed through the first opening and positioned within the interior space.

6. The method of claim 1 wherein the lead includes a plurality of openings at selected locations along the lead body, and the pressure transducer may be deployed out through any of the plurality of openings.

7. A method of optimizing implant parameters for an implantable cardiac rhythm management system including an implantable pulse generator and a coronary venous lead, the coronary venous lead including: an elongate, flexible lead body made of an electrically insulative material, the body having a proximal end and a distal end, the body being sized to permit the distal end to be advanced through a right atrium and a coronary sinus and into a first coronary vein adjacent to a left ventricle of a patient's heart; a first opening in the body at a point intermediate the proximal and distal ends; a lumen extending longitudinally within the lead body and in communication with the first opening; and at least one pace/sense electrode coupled to the body proximate the distal end, the method comprising:
    positioning the electrode within the first coronary vein adjacent the left ventricle;
    operatively coupling the electrode to the implantable pulse generator or a pacing system analyzer device;
    deploying a pressure transducer through the lumen and adjacent the first opening in the lead;
    generating an acute baseline pressure waveform based on an output signal from the pressure transducer over a plurality of cardiac cycles;
    applying an electrical stimulus to the left ventricle through the electrode using the implantable pulse generator or the pacing system analyzer; and
    adjusting one or more CRM system parameters while monitoring changes in the pressure waveform relative to the baseline.

8. The method of claim 7 wherein the lead includes a plurality of openings at selected locations along the lead body, and the pressure transducer may be deployed adjacent any of the plurality of openings.

9. The method of claim 7 wherein adjusting one or more CRM system parameters includes relocating the electrode to a second location within the first coronary vein, the second coronary vein, or a third coronary vein.

10. The method of claim 7 wherein adjusting one or more CRM system parameters includes adjusting A-V delay and/or V-V delay.

11. The method of claim 7 wherein adjusting one or more CRM system parameters further includes adjusting one or more CRM system parameters while monitoring changes in mechanical timing in addition to changes in the pressure waveform relative to the baseline.

* * * * *